United States Patent [19]

Hobler et al.

[11] 3,991,883
[45] Nov. 16, 1976

[54] METHOD AND APPARATUS FOR IDENTIFYING A BOTTLE

[75] Inventors: Ross L. Hobler, Elmira; Nelson H. Bryant, Ithaca, both of N.Y.

[73] Assignee: Powers Manufacturing Incorporated, Elmira, N.Y.

[22] Filed: July 17, 1975

[21] Appl. No.: 596,697

Related U.S. Application Data

[63] Continuation of Ser. No. 467,702, May 6, 1974, abandoned.

[52] U.S. Cl. .......................... 209/73; 209/111.7 T; 250/223 B; 235/61.11 E
[51] Int. Cl.² ............................................ B07C 5/34
[58] Field of Search ............... 209/72, 111.7, 111.5, 209/73; 250/223 R, 223 B, 224; 356/106 LR, 240; 235/61.11 E

[56] References Cited
UNITED STATES PATENTS

| | | | |
|---|---|---|---|
| 3,690,456 | 9/1972 | powers, Jr. | 209/111.7 X |
| 3,745,254 | 7/1973 | Vargo | 235/61.11 E |
| 3,745,314 | 7/1973 | Mathias | 250/223 B |
| 3,770,969 | 11/1973 | Ansevin et al. | 250/223 B |

Primary Examiner—Allen N. Knowles
Attorney, Agent, or Firm—Seidel, Gonda & Goldhammer

[57] ABSTRACT

Bottles transparent to a laser beam are molded with marks on a wall thereof. The marks serve to identify each bottle with its respective mold. The bottles are rotated and moved in a procession through an inspection area where a laser beam is directed through the wall of each bottle so that the beam strikes each of the marks. Each mark causes the laser beam to spread as the beam strikes the mark and passes through the bottle. As the laser beam emerges from the bottle, the beam is directed to a sensor which generates a digital output signal corresponding to the distribution of the marks on the bottle. Any bottle may be ejected from the procession according to the sensor output.

14 Claims, 11 Drawing Figures

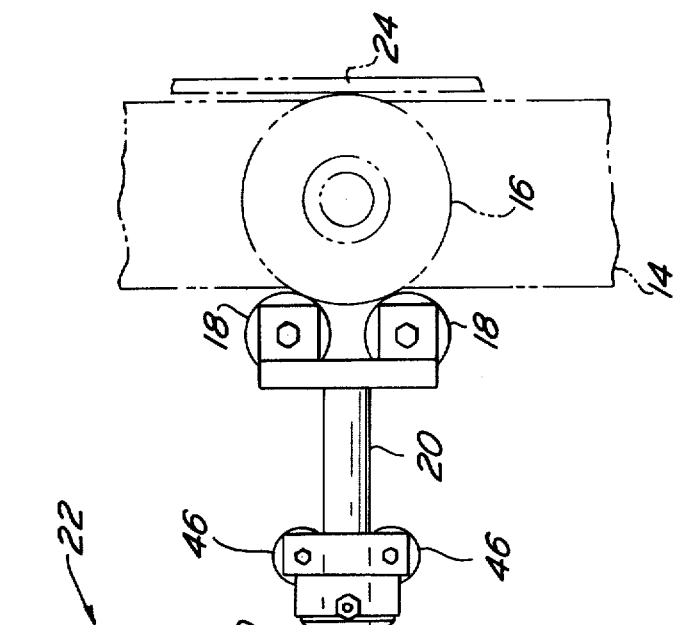
FIG. 4
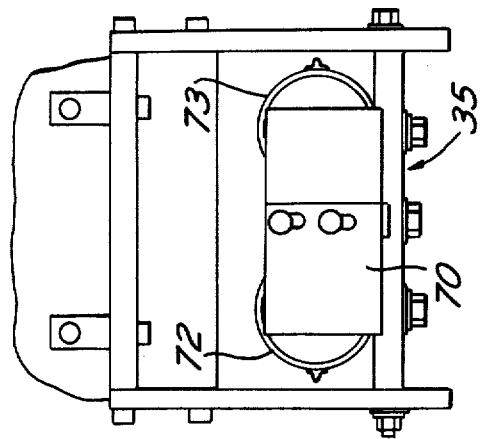
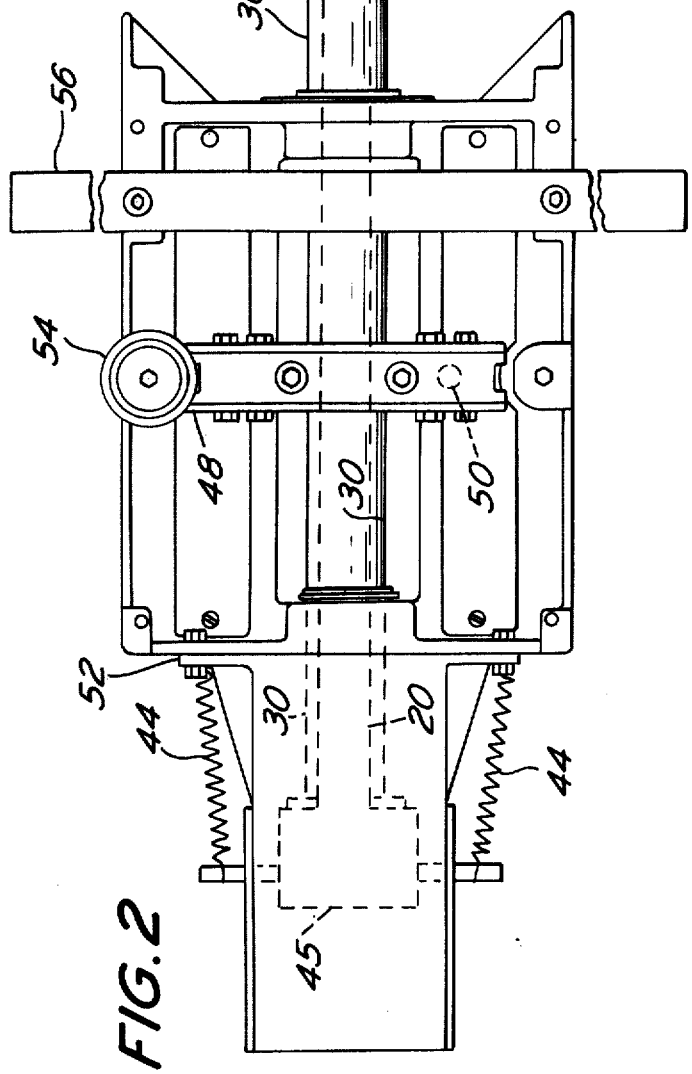
FIG. 2

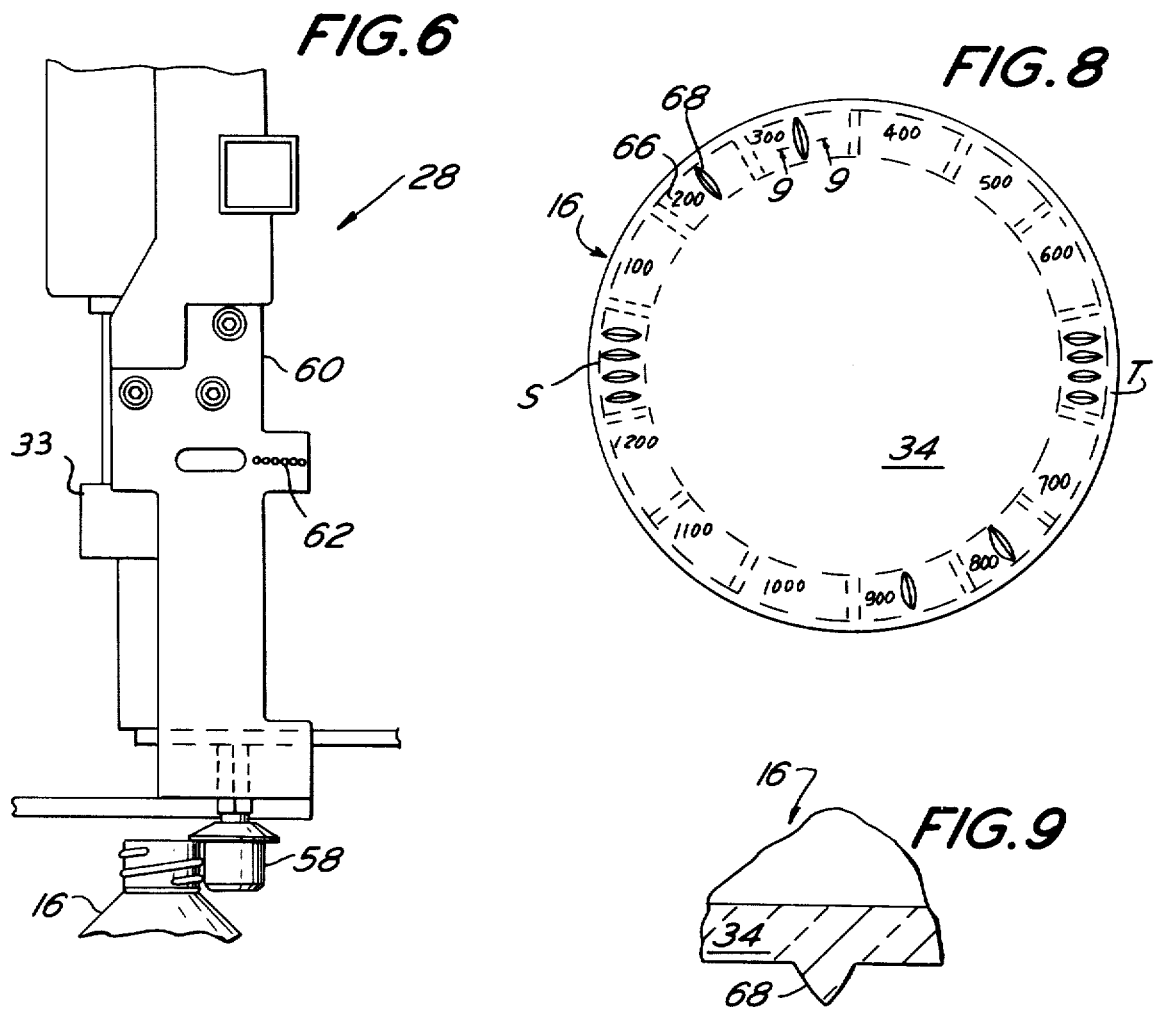
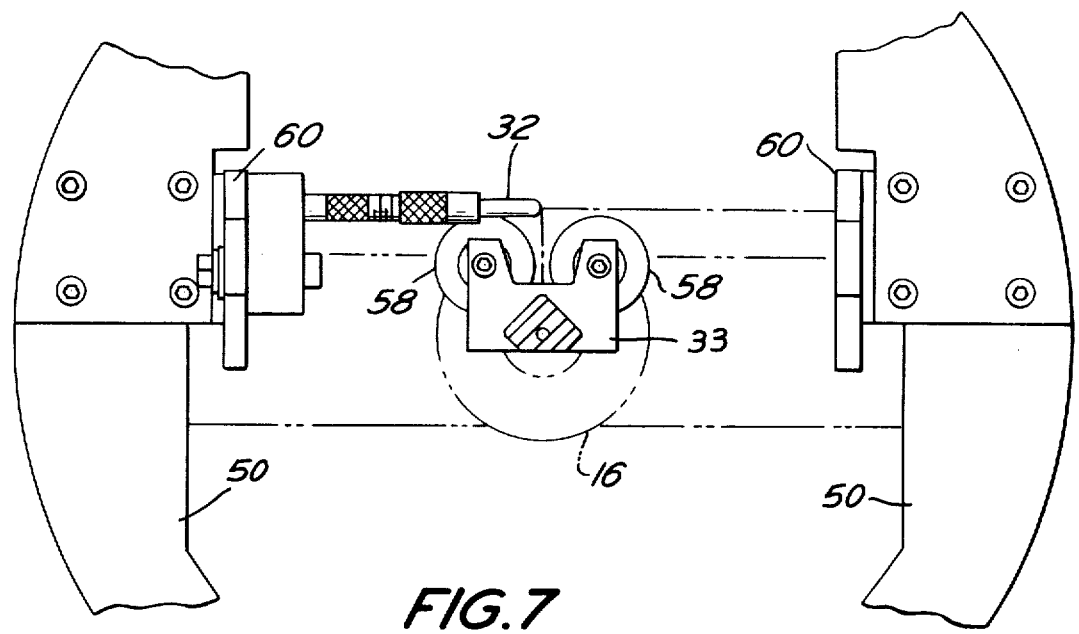

METHOD AND APPARATUS FOR IDENTIFYING A BOTTLE

This is a continuation of application Ser. No. 467,702, filed May 6, 1974, now abandoned.

BACKGROUND OF THE INVENTION

The present invention relates to a method and apparatus for automatically identifying a bottle which is transparent to a laser beam according to the mold in which it was made. More specifically, the invention relates to a method and apparatus for automatically identifying and ejecting defectively formed bottles.

It is well-known in the art to automatically identify a container, regardless of transparency, by a variety of surface markings placed on the exterior of the container. Depending upon the purpose for which an apparatus has been designed, these surface markings can indicate any of a number of events. For example, U.S. Pat. No. 2,647,799 discloses a machine which sorts a procession of metal cans according to the contents of the cans. The contents are denoted by the application of non-reflective stripes on the exterior of the can. More specifically, the precise location of a non-reflective stripe connotes the nature of the contents of the can.

In the sorting machine of said patent, a light source and detector pair scans a limited area of the can exterior. All possible locations for a stripe are scanned by a series of such source-detector pairs. Accordingly, a multiplicity of light sources and detectors is required in order to scan all possible stripe locations. The machine, then, requires a multiplicity of inspection stations to identify each container. The identification of a container by such a machine is unduly time-consuming and does not lend itself for use with transparent bottles since the exterior of such a bottle is non-reflective.

Techniques and devices for automatically identifying a transparent bottle are also known in the art. One such technique is to mark the exterior of the bottle according to the mold in which that bottle was formed and to mechanically count the number of marks appearing on the bottle. For example, in U.S. Pat. No. 3,301,396 for "Method of and Apparatus for Classifying Glass Bottles" there is described a machine for automatically identifying the source of a glass bottle according to the number of surface markings appearing on the bottle exterior. In particular, a number of projections is formed on the bottom of the bottle. Bottles having different numbers of projections are formed in respectively different molds. The mere number of projections, therefore, identifies the source of the bottle. A processing of the bottles is fed through a plurality of inspection stations, each of which contains a set of mechanically operated scanning switches which control an ejection channel. Upon reaching the inspection station, the bottle — and therefore the entire procession — is stopped and the scanning switches are brought into physical contact with the bottom of the bottle. With the bottle stationary, the switches rotatably contact the projections on the bottom of the bottle. The switches, then, provide a count of the total number of projections. Since the number of projections corresponds to a particular mold, the count serves to identify the source of the bottle. In the course of computing the number of projections, the spatial distribution of the projections is immaterial; the switches respond identically to all bottles having the same number of projections regardless of the location and spacing thereof.

A chief disadvantage of the device described in U.S. Pat. No. 3,301,396 is the necessity for stopping each bottle at the inspection station. That is, a considerable amount of time is wasted by interrupting the procession to permit the inspection of each bottle. A further disadvantage of the apparatus is that the number of projections which can appear on the bottle exterior is limited by the available surface area and the size of the projections. Accordingly, there is a practical limit to the number of projections which can be counted. As a result, the machine described in said patent can be used to identify a bottle with a limited number of molds. A plant using large numbers of molds, then, will require several of these machines. Furthermore, since the projections must extend considerably beyond the surface of the bottom of the bottle to contact the scanning switches, the projections themselves may introduce defects in the bottle due to strain in the glass surface skin; and a projection may fail to operate a switch due to bulge or sag in the bottom of the bottle, causing an erroneous count and a mistaken identification.

A principal advantage of the present invention is that the bottles are inspected for identification with a preselected mold without interrupting the flow of the main procession toward the packing station.

Another advantage of the invention is that only one inspection station is required to identify each bottle in the procession and a single laser and sensor pair is used to inspect the entire procession.

An additional advantage is that a single machine can be used to identify a bottle with a large number of molds.

Further advantages appear hereinafter.

BRIEF SUMMARY OF THE INVENTION

Briefly, in the present invention, a bottle which is transparent to a laser beam is provided with marks on a wall thereof. A laser beam is directed to the wall of the bottle and the bottle is rotated with respect to the laser beam so that the beam strikes each of the marks. Each mark causes the laser beam to spread as the beam strikes the mark and passes through the wall of the bottle. As the beam emerges from the bottle it is directed to a sensor which receives the beam only if it has struck a mark. The sensor generates a digital output signal corresponding to the distribution of marks on the bottom wall of the bottle. Any bottle may be ejected from the procession according to the sensor output.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 2 is a bottom plan view of a horizontally movable carriage and plunger.

FIG. 4 is a front view of the sensor in FIG. 3 taken along line 4.

FIG. 6 is a front view of a laser aperture plate.

FIG. 7 is a top plan view of a movable carriage and neck rollers.

FIG. 8 is a bottom plan view of the bottle.

FIG. 9 is a cross-section of a timing mark on the bottle bottom.

DETAILED DESCRIPTION OF THE INVENTION

Figure 1:
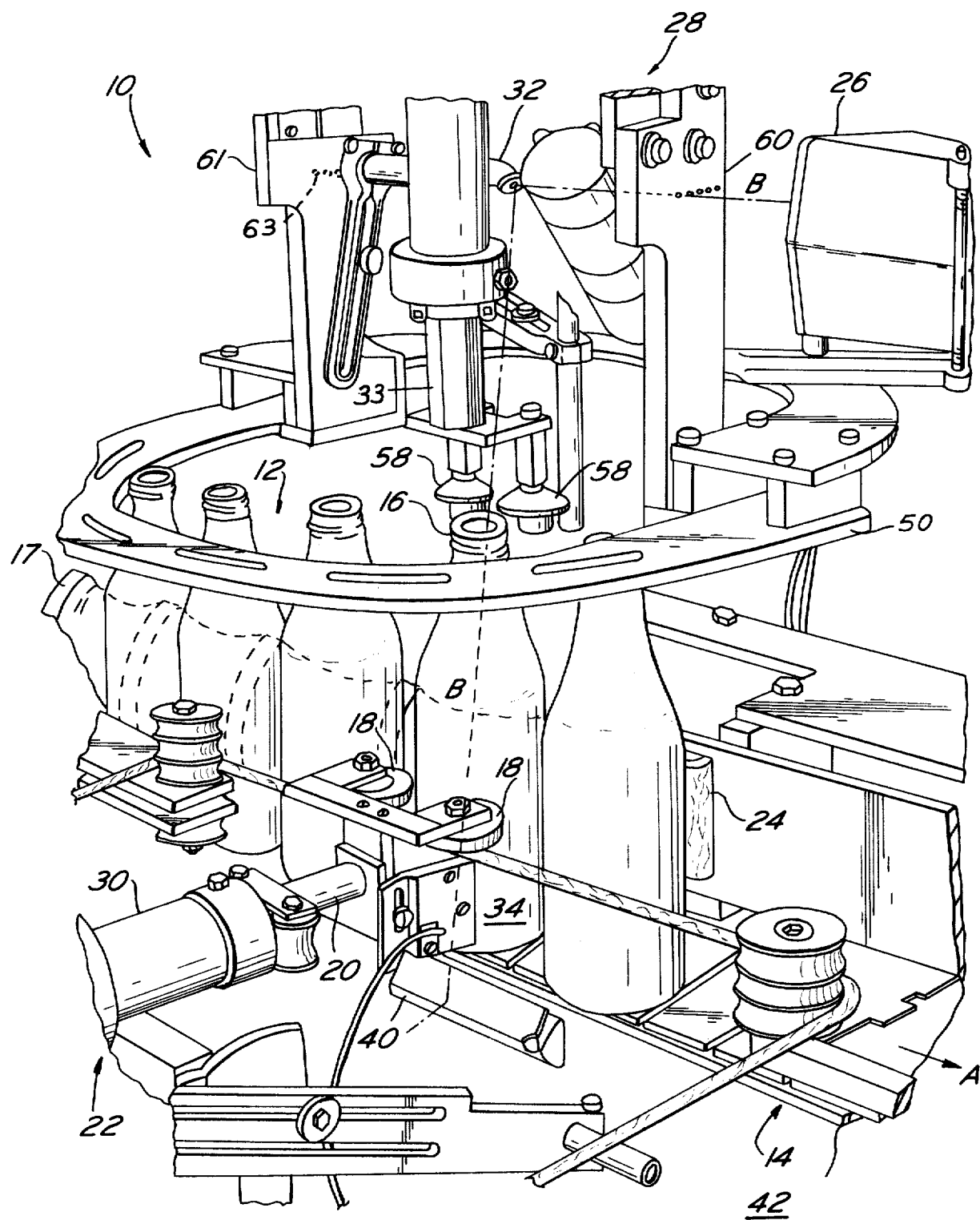
FIG. 1 is a perspective view of the apparatus.

Referring to the drawings, wherein like numerals indicate like elements, there is shown in FIG. 1 an apparatus for identifying bottles which are transparent to a laser beam constructed in accordance with the principles of the present invention and designated generally as 10. A main procession of bottles 12 is shown being transported by a linear conveyor 14 of conventional construction. The bottle 16 in the procession 12 are uniformly spaced apart by screw conveyor 17 and transported by the inspection area by a linear conveyor 14 as described in my U.S. Pat. No. 3,557,950 "Photo-Electric Crack Detector For Glass Bottles."

As the bottle 16 enters the inspection area, it is engaged by a pair of spaced rollers 18 rotatably mounted on a horizontally disposed plunger 20. As shown in FIG. 2, the plunger 20 is mounted for reciprocating movement to and from the conveyor 14 on a horizontally movable carriage 22. The carriage 22 is mounted for reciprocation in a path parallel to the direction of movement of conveyor 14, designated by arrow A in FIG. 1. At the beginning of the stroke of carriage 22 in the direction of arrow A, the plunger 20 is cammed or biased towards the bottle 16. At the conclusion of the stroke, plunger 20 is cammed or biased away from bottle 16, and carriage 22 then returns to its initial position.

The carriage 22 moves in synchronism with screw conveyor 17 and linear conveyor 14. During the forward stroke of carriage 22, rollers 18 engage bottle 16 without interrupting the linear motion of bottle 16 in the direction of arrow A. The rollers 18 press bottle 16 against a rotator belt 24. The structure of the rotator belt 24 is described in detail in my U.S. Pat. No. 3,690,456 for a "Glass Container Crack Detector." Preferably, the belt 24 moves in the same direction as conveyor 14. As a result, bottle 16 is caused to rotate about its axis as it traverses the inspection area. Rotator belt 24 may also move in a direction opposite to that of conveyor 14 to cause bottle 16 to rotate but movement in the same direction as conveyor 14 is preferred to facilitate the discharge of defective bottles that have passed through the inspection area. The belt 24 is driven by a variable speed motor so that the speed of rotation of bottle 16 may be adjusted as desired. It is preferred that belt 24 move at a speed sufficient to cause bottle 16 to rotate through at least 360° as it traverses the inspection area.

A second carriage 28 is positioned above conveyor 14 and is mounted for reciprocation in a horizontal direction parallel to arrow A. See FIG. 1. Specifically, carriages 22 and 28 move in synchronism through the inspection area at a constant speed, and return to their initial positions at a substantially sinusoidal rate after traversing the inspection area. A vertical plunger 33 is mounted on carriage 28 for vertical reciprocating movement to and from the neck of bottle 16. In particular, the plunger 33 moves downwardly at the beginning of the inspection area and upwardly at the end of the inspection area. The mechanism for synchronizing the reciprocating motion of carriage 22 and 28 as well as the mechanism for moving the plunger 33 are described in detail in my U.S. Pat. No. 3,397,704 for an "Aperture Gauging and Sorting Device."

As shown in FIG. 1, a pair of spaced neck rollers 58 is rotatably supported by plunger 33. Neck rollers 58 hold bottle 16 downwardly against any vertical forces generated by rotation of the bottle 16 as described in my U.S. Pat. No. 3,690,455. The neck rollers 58 are positioned to contact the neck of bottle 16 when rollers 18 press bottle 16 against rotator belt 24. It is preferred that neck rollers 58 be made from a rubber or plastic material to prevent damage to the neck of bottle 16 upon contact therewith.

A ring 50 is mounted on carriage 28 and depends therefrom. The ring 50 may be two semi-circular segments at the same or different elevations as described in my U.S. Pat. No. 3,690,456 for a "Glass Container Crack Detector."

Figure 5:
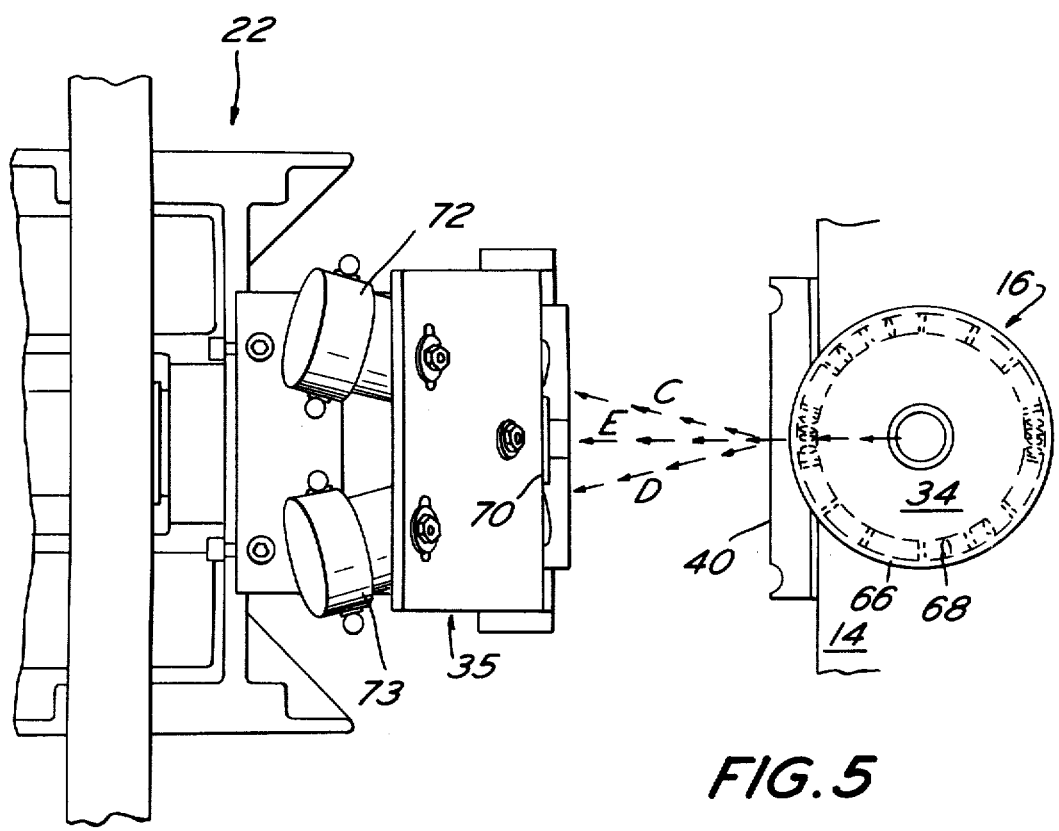
FIG. 5 is a bottom plan view of the sensor in FIG. 3 taken along line 5.

A laser 26 is mounted on second carriage 28 so that the position of laser 26 with respect to carriage 28 is adjustable. In addition, a mirror 32 is mounted on the carriage 28 and is positioned to direct the laser beam, indicated by the broken line B in FIG. 1, through the opening in the neck of bottle 16 and to the bottom wall 34 thereof as bottle 16 moves through the inspection area. See FIG. 3. A sensor 35 is securely mounted on carriage 22 and is positioned to detect the laser beam as it emerges from bottom wall 34 of bottle 16. The laser beam is directed by mirror 32 shown in FIG. 1, to the annular sectors 66 of bottom wall 34 as shown in FIGS. 5 and 8.

Figure 3:
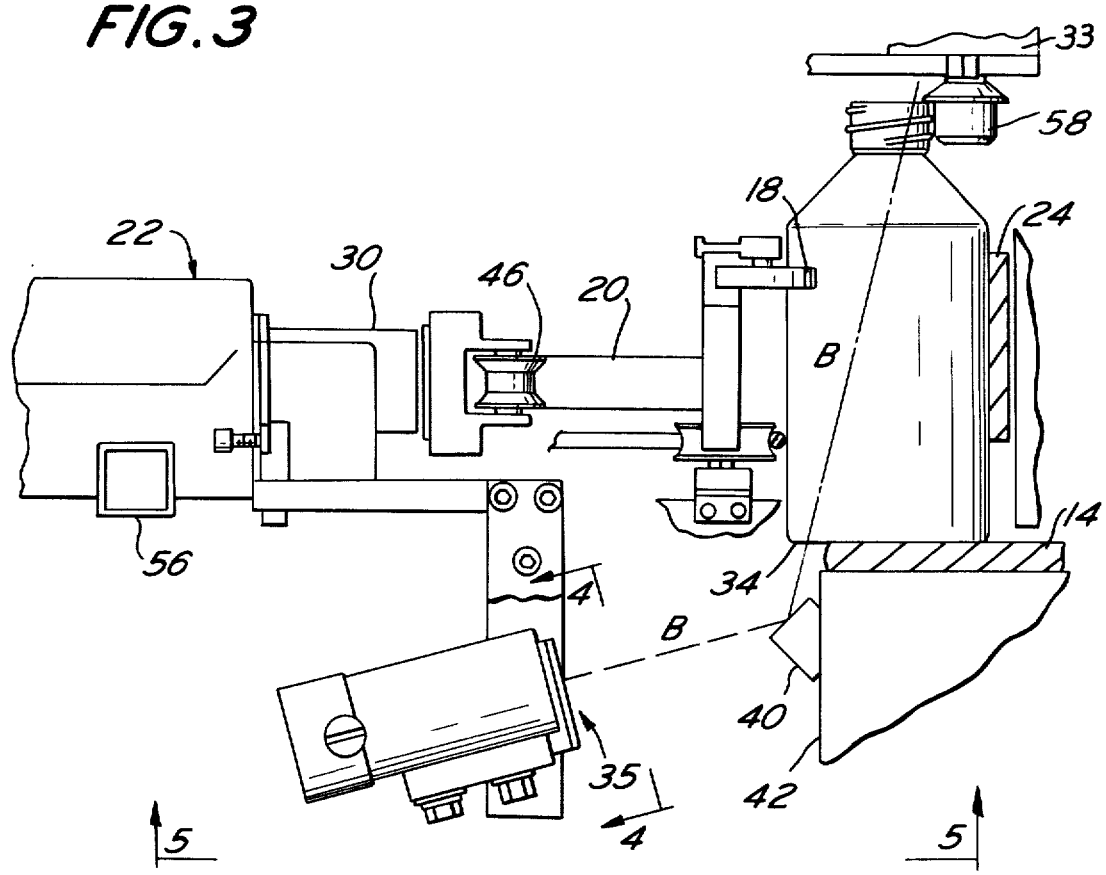
FIG. 3 is a side view of the horizontal plunger, the sensor and the laser beam.

The annular sectors 66 are provided with marks 68 which disperse the laser beam emerging from bottom wall 34 as described more particularly hereinafter. As shown in FIGS. 1 and 3, a mirror 40 is securely mounted on a stationary support member 42 positioned alongside conveyor 14. The mirror 40 is sufficiently long to intercept the laser beam and direct it to sensor 35 over the length of the inspection area. Thus, as carriages 22 and 28 move in synchronism with bottle 16 through the inspection area, the laser beam is directed through the bottom wall 34 of bottle 16 and reflected by mirror 40 to sensor 35.

Referring to FIG. 2, plunger 20 is guided for reciprocating movement by a sleeve 30 and guide rollers 46 rotatably mounted thereon. Springs 44 bias plunger 20 towards conveyor 14 as the carriage 22 traverses the inspection area in the direction of arrow A. A yoke bearing plate 48 is securely mounted on carriage 22 and is reciprocated in a direction toward and away from conveyor 14 by a crank roller 50 shown in FIG. 3 as a dotted circle. The lateral reciprocating movement of plate 48 is generated by means of two mechanisms, one horizontal and one vertical, essentially as disclosed in my U.S. Pat. No. 3,387,704.

Plunger 20, at its distal end with respect to conveyor 14, is fixed to a head plate 45. The head plate 45 is connected by springs 44 to a support member 52 on carriage 22. Springs 44 provide a biasing force which urges the head plate 45 against the sleeve 30 and therefore biases the plunger 20 toward conveyor 14. However, when rollers 18 first contact the bottle 16 as it enters the inspection area, the bottle pushes the plunger 20 away from conveyor 14 and the springs 44 expand to accommodate motion of the head plate 45 away from sleeve 30.

The reciprocating motion of plunger 20 toward and away from a bottle 16 is generated by crank roller 50 which drives yoke bearing plate 48. Sleeve 30 is fixed to bearing plate 48 and, at its distal end with respect to conveyor 14, abuts the head plate 45 which is fixed to plunger 20. As sleeve 30 is moved to the right in FIG. 2 by crank roller 50 and bearing plate 48, the head plate 45 follows sleeve 30 due to contraction of the springs 44. Since plunger 20 is coupled to head plate 45, it too is urged towards conveyor 14 so that rollers 18 may engage bottle 16. When sleeve 30 is moved in a direction away from conveyor 14, (from right to left to FIG. 2), sleeve 30 urges head plate 45 and plunger 20 in the same direction. Accordingly, rollers 18 lose contact with bottle 16.

The reciprocating motion of plunger 20 toward and away from conveyor 14 is synchronized with the motion of carriage 22. Carriage 22 moves reciprocatingly, parallel to conveyor 14 over the length of the inspection area. The reciprocating motion of carriage 22 is generated by cam follower 54 mounted thereon which cooperates with an annular cam track (not shown). A transverse member 56, securely mounted on carriage 22, rides between a plurality of rollers (not shown) to guide carriage 22 along a path parallel to conveyor 14 as carriage 22 reciprocates in response to a camming action on cam follower 54. Therefore, at the beginning of the stroke of carriage 22 in the direction of arrow A, sleeve 30 is cammed towards conveyor 14 and springs 44 urge plunger 20 towards bottle 16. Rollers 18 engage bottle 16 as it enters the inspection area and embrace bottle 16 as it is inspected. At the end of the stroke of carriage 22, sleeve 30 is cammed away from conveyor 14, pushing head plate 45 and plunger 20 away from bottle 16. Rollers 20 release bottle 16 and carriage 22 returns to its initial position so that the process may be repeated with the next bottle 16. All of the above is accomplished without interrupting the continuous motion of each bottle 16 through the inspection area.

Referring to FIGS. 1 and 6, a pair of laser aperture plates 60 and 61 are mounted on ring 50 on carriage 28 and are positioned in the path of the laser beam. As shown in detail in FIG. 6, the aperture plates 60 and 61 are provided with rows of apertures 62 and 63, respectively. The apertures 62 of plate 60 are aligned with the apertures 63 of plate 61 and laser 26 is positioned so that the laser beam passes through one pair of the aligned apertures 62 and 63. Mirror 32 is then fastened to aperture plate 61 and is positioned to reflect the laser beam so that the reflected beam lies in a vertical plane perpendicular to conveyor 14 and strikes the annular sectors 66 of bottom 34, as shown in FIGS. 3 and 8. Mirror 32 is positioned to reflect the laser beam so that it passes between the neck rollers 58 and through the opening in the neck of bottle 16, as shown in FIGS. 1 and 3. Thus, the beam travels freely, not striking any part of bottle 16, until it impinges on an annular sector 66 of bottom wall 34.

Referring now to FIG. 8, there is shown in detail the feature of a bottom all 34 of bottle 16 which is used in the present invention. Specifically, in the preferred embodiment shown, a plurality of marks 68 are distributed in the annular sectors 66 to provide an optical signal which represents a binary number. However, it should be understood that for purposes of the invention the mark 68 could be distributed circumferentially about the side walls of the bottle 16, the positioning of the sensor 35 and mirrors 32 and 40 being modified accordingly. The binary number identifies the mold in which the bottle 16 was formed. As shown, two annular sectors denoted S and T, (the "timing sectors") are diametrically opposed and are provided with a plurality of marks 68. Timing sectors S and T serve to initiate or terminate, resepctively, the detection process described hereinafter.

On either side of the diameter connecting timing sectors S and T, there are shown an equal number of annular sectors 66 each of which are provided with no more than one timing mark 58. Annular sectors 66 above the diameter connecting sectors S and T are denoted as 100, 200, 300, 400, 500 and 600; and the annular sectors 66 below are denoted as 700, 800, 900, 1000, 1100 and 1200. The marks 68 are arranged so that pairs of sectors 66 are marked identically. Thus, sectors 100 and 700 ar marked identically and so are sectors 200 and 800; 300 and 900; 400 and 1000; 500 and 1100; and 600 and 1200. The absence of a timing mark 68 in a sector 66 connotes a binary 0 while the presence of a mark 68 connotes a binary 1. Traversing the annular sectors 66 in a clockwise direction, annular sectors 100, 200, 300, 400, 500 and 600 define the binary number 011000, as do sectors 700, 800, 900, 1000, 1100 and 1200. By changing the distribution of the timing marks 68, a multiplicity of binary numbers is defined. For example, in FIG. 8, sixty-four binary numbers may be defined using six annular sectors 66. This is shown below in Table 1 where each annular sector 100, 200, 300, 400, 500, and 600 has been assigned a unique position in a six digit binary number.

TABLE I

BINARY NUMBERS REPRESENTED BY TIMING MARKS

| Decimal Equiv. | Annular Sector | | | | | |
|---|---|---|---|---|---|---|
| | 100 | 200 | 300 | 400 | 500 | 600 |
| 1 | 1 | 0 | 0 | 0 | 0 | 0 |
| 2 | 0 | 1 | 0 | 0 | 0 | 0 |
| 3 | 1 | 1 | 0 | 0 | 0 | 0 |
| 4 | 0 | 0 | 1 | 0 | 0 | 0 |
| 5 | 1 | 0 | 1 | 0 | 0 | 0 |
| 6 | 0 | 1 | 1 | 0 | 0 | 0 |
| 7 | 1 | 1 | 1 | 0 | 0 | 0 |
| 8 | 0 | 0 | 0 | 1 | 0 | 0 |
| 9 | 1 | 0 | 0 | 1 | 0 | 0 |
| 10 | 0 | 1 | 0 | 1 | 0 | 0 |
| 11 | 1 | 1 | 0 | 1 | 0 | 0 |
| 12 | 0 | 0 | 1 | 1 | 0 | 0 |
| 13 | 1 | 0 | 1 | 1 | 0 | 0 |
| 14 | 0 | 1 | 1 | 1 | 0 | 0 |
| 15 | 1 | 1 | 1 | 1 | 0 | 0 |
| 16 | 0 | 0 | 0 | 0 | 1 | 0 |
| 17 | 1 | 0 | 0 | 0 | 1 | 0 |
| 18 | 0 | 1 | 0 | 0 | 1 | 0 |
| 19 | 1 | 1 | 0 | 0 | 1 | 0 |
| 20 | 0 | 0 | 1 | 0 | 1 | 0 |
| 21 | 1 | 0 | 1 | 0 | 1 | 0 |
| 22 | 0 | 1 | 1 | 0 | 1 | 0 |
| 23 | 1 | 1 | 1 | 0 | 1 | 0 |
| 24 | 0 | 0 | 0 | 1 | 1 | 0 |
| 25 | 1 | 0 | 0 | 1 | 1 | 0 |
| 26 | 0 | 1 | 0 | 1 | 1 | 0 |
| 27 | 1 | 1 | 0 | 1 | 1 | 0 |
| 28 | 0 | 0 | 1 | 1 | 1 | 0 |
| 29 | 1 | 0 | 1 | 1 | 1 | 0 |
| 30 | 0 | 1 | 1 | 1 | 1 | 0 |
| 31 | 1 | 1 | 1 | 1 | 1 | 0 |
| 32 | 0 | 0 | 0 | 0 | 0 | 1 |
| 33 | 1 | 0 | 0 | 0 | 0 | 1 |
| 34 | 0 | 1 | 0 | 0 | 0 | 1 |
| 35 | 1 | 1 | 0 | 0 | 0 | 1 |
| 36 | 0 | 0 | 1 | 0 | 0 | 1 |
| 37 | 1 | 0 | 1 | 0 | 0 | 1 |
| 38 | 0 | 1 | 1 | 0 | 0 | 1 |
| 39 | 1 | 1 | 1 | 0 | 0 | 1 |

TABLE 1-continued

BINARY NUMBERS REPRESENTED BY TIMING MARKS

| Decimal Equiv. | Annular Sector | | | | | |
|---|---|---|---|---|---|---|
| 40 | 0 | 0 | 0 | 1 | 0 | 1 |
| 41 | 1 | 0 | 0 | 1 | 0 | 1 |
| 42 | 0 | 1 | 0 | 1 | 0 | 1 |
| 43 | 1 | 1 | 0 | 1 | 0 | 1 |
| 44 | 0 | 0 | 1 | 1 | 0 | 1 |
| 45 | 1 | 0 | 1 | 1 | 0 | 1 |
| 46 | 0 | 1 | 1 | 1 | 0 | 1 |
| 47 | 1 | 1 | 1 | 1 | 0 | 1 |
| 48 | 0 | 0 | 0 | 0 | 1 | 1 |
| 49 | 1 | 0 | 0 | 0 | 1 | 1 |
| 50 | 0 | 1 | 0 | 0 | 1 | 1 |
| 51 | 1 | 1 | 0 | 0 | 1 | 1 |
| 52 | 0 | 0 | 1 | 0 | 1 | 1 |
| 53 | 1 | 0 | 1 | 0 | 1 | 1 |
| 54 | 0 | 1 | 1 | 0 | 1 | 1 |
| 55 | 1 | 1 | 1 | 0 | 1 | 1 |
| 56 | 0 | 0 | 0 | 1 | 1 | 1 |
| 57 | 1 | 0 | 0 | 1 | 1 | 1 |
| 58 | 0 | 1 | 0 | 1 | 1 | 1 |
| 59 | 1 | 1 | 0 | 1 | 1 | 1 |
| 60 | 0 | 0 | 1 | 1 | 1 | 1 |
| 61 | 1 | 0 | 1 | 1 | 1 | 1 |
| 62 | 0 | 1 | 1 | 1 | 1 | 1 |
| 63 | 1 | 1 | 1 | 1 | 1 | 1 |

Each binary number has a decimal equivalent as shown in Table 1. Assuming that the binary number 000000 (decimal 0) is not used, there are sixty-three arrangements for the marks 68. Accordingly, any bottle 16 may be identified with any one of sixty-three different molds, each of the sixty-three possible arrangements of marks 68 on any bottle 16 being formed by an associated mold. The number of marks 68, of itself, does not identify a bottle 16 with a particular mold. Instead, the distribution of the marks 68 on the bottom 34 of bottle 16 determines the identity of the mold in which bottle 16 was made. For example, as shown in Table 1 above, a single mark 68 may be placed in any of the six annular sectors 100, 200, 300, 400, 500 and 600 to produce six different binary numbers (decimal equivalents 1, 2, 4, 8, 16, 32). If the number of timing marks 68 were merely counted as in U.S. Pat. No. 3,301,396, an erroneous identification would result. In addition, as compared to the method described in said patent, the method of the present invention permits the identification of a bottle with a significantly greater number of molds, avoiding the need for a multiplicity of machines in a plant which employs large numbers of molds.

In the preferred embodiment shown in FIG. 8, the marks 68 are distributed among the sectors 66 above and below the diameter connecting sectors S and T so that each group of sectors 66 above and below said diameter defines the same binary number when traversed in like directions. Thus, either timing sector S and T initiates the detection process and regardless of which timing sector, S or T, initiates the detection process the binary number detected will be the same due to the paired distribution of the marks 68 (previously discussed).

Referring now to FIGS. 3 and 5, the precise manner in which the marks 68 produce the desired optical effect will be described. In FIG. 5, bottle 16 is shown being transported through the inspection area on conveyor 14. As previously mentioned, the rollers 18 engage the bottle 16 and urge it against rotator belt 24 causing bottle 16 to rotate as it traverses the inspection area. The rotator belt 24 is positioned so that the bottom 34 of bottle 16 overhangs the edge of conveyor 14 closest to sensor 35. More specifically, the annular sectors 66 of bottom 34 are exposed beyond the edge of conveyor 14 as bottle 16 rotates. The laser beam passes through the opening in the neck of bottle 16 and strikes each annular sector 66 as it is exposed beyond the edge of conveyor 14. The beam passes through sector 66 and strikes mirror 40 which directs the beam to sensor 35. Sensor 35 includes a sensor mask 70 and two photocells 72 and 73. Depending on the beamwidth of the laser beam reflected from mirror 40, the sensor 35 generates a digital output signal corresponding to either a binary 0 or 1.

If the laser beam strikes an annular sector 66 which contains no mark 68 the beam will pass through sector 66, strike mirror 40 and travel on to sensor mask 70 shown in FIG. 4. The mask 70 blocks the beam, represented by arrows E in FIG. 5, from striking the pair of photocells 72 and 73. Therefore, the photocells 72 and 73 do not receive the laser beam when sector 66 has no mark 68 located therein, and they generate a digital signal representing a binary 0. On the other hand, if sector 66 is provided with a mark 68 the laser beam will strike mark 68 and fan out as shown by arrows C and D in FIG. 5. The physical dimensions of mark 68 are such that the width of the laser beam emerging from mark 68 is greater than the width of the mask 70, at sensor 35. As a result, photocells 72 and 73 will detect the beam. The speed with which bottle 16 rotates with respect to the laser beam is controlled by rotator belt 24 and is set so that every annular sector 66 on a semicircle between timing sectors S and T will be presented to the laser beam as bottle 16 is rotated and transported through the inspection area. Therefore, the speed of rotator belt 24 is set so that the bottle 16 rotates at least 360° as it is transported through the inspection area. Those sectors 66 having marks 68 will cause photocells 72 and 73 to generate a digital signal which indicates the presence of the mark 68 by a binary 1. But if sector 66 has no mark 68 therein, photocells 72 and 73 will not receive the laser beam and they will generate a digital signal which indicates the absence of mark 68 by a binary 0.

As mentioned previously, carriage 28 moves in synchronism with carriage 22 and bottle 16 as bottle 16 traverses the inspection area. Since mirror 32 is securely mounted on carriage 28 and sensor 35 is securely mounted on carriage 22, mirror 32 and sensor 35 move in synchronism with each other and with bottle 16 as it is rotated and transported through the inspection area. Accordingly, the binary number characterized by the marks 68 in a semi-circle between timing sectors S and T will be detected by sensor 35.

In the preferred embodiment shown in FIG. 9, mark 68 is in the shape of a prism projecting outwardly from the underside of bottom wall 34 of bottle 16. However, mark 68 may take any shape so long as it causes the laser beam to spread in the manner previously described. For example, mark 68 may also be a depression in bottom wall 34, and shaped as a prism.

Figure 10:
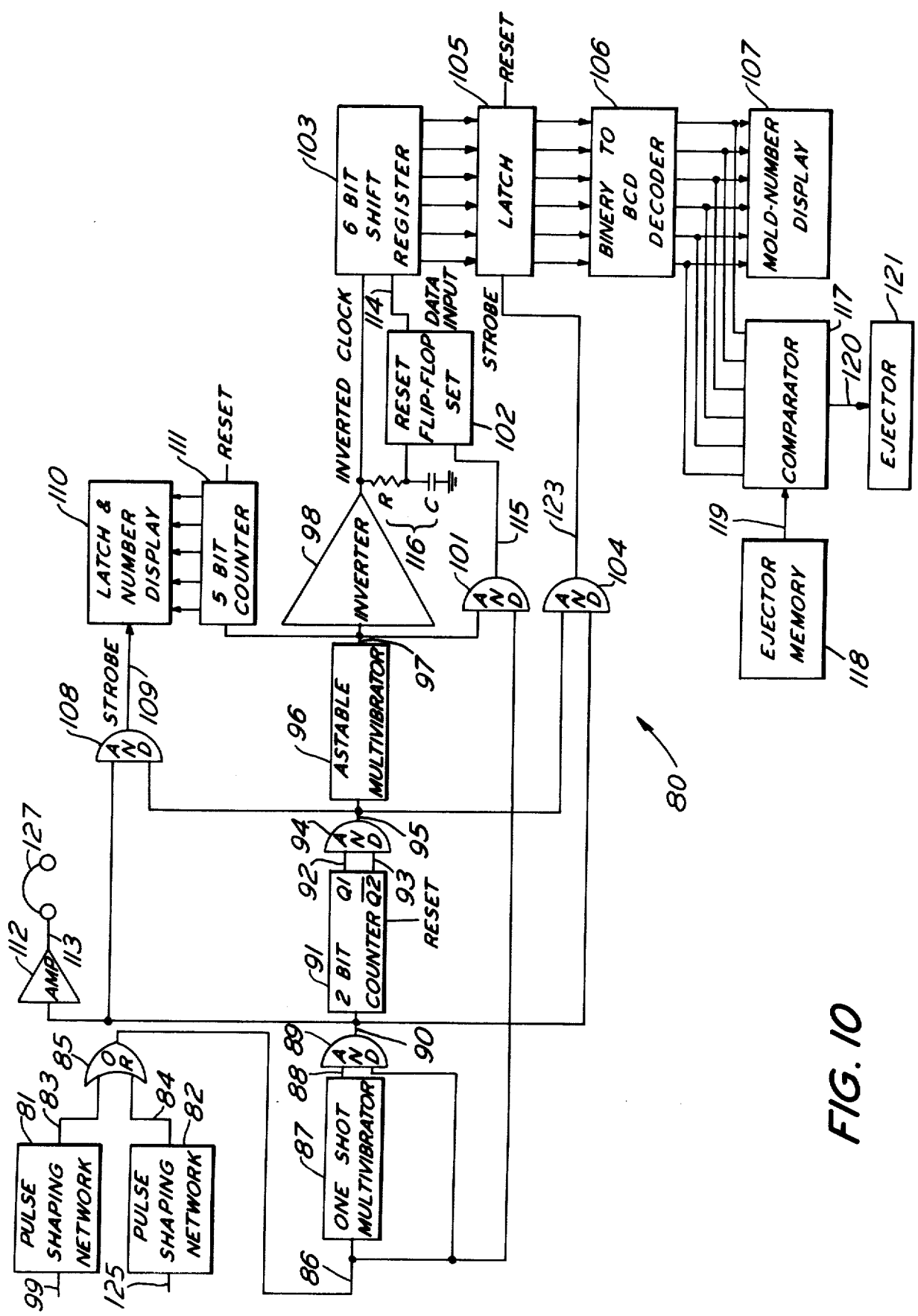
FIG. 10 is a block diagram of the electronic control system.

An electrical control circuit shown in FIG. 10, and designated generally as 80, responds to the electric signals generated by photocells 72 and 73. The timing sectors S and T initiate and terminate the detection process with respect to a particular bottle 16 according to a form of pulse width discrimination described herein. As mentioned previously and as shown in FIG. 8, timing sectors S and T are provided with a greater number of marks 68 than the other annular sectors 66.

In timing sectors S and T, the marks 68 are spaced so that the laser beam is continuously received by the photocells 72 and 73 over the time period required to rotate the bottle 16 through the arcuate distance spanned by sector S or T. Photocells 72 and 73, then, will generate an electric signal corresponding to timing sector S or T which has a pulse width greater than the pulse width of an electric signal generated in response to any other sector 66 having only a single mark 68.

The electric control circuit 80 discriminates between the pulse widths of the electric signals generated by photocells 72 and 73. The circuit 80 does not begin the detection process until either timing sector S or T causes a relatively long pulse to appear at the output of photocells 72 and 73. And once begun, the detection process does not terminate until photocells 72 and 73 receive a second pulse of relatively long duration. For example, if timing sector S produces the first relatively long pulse to begin the detection process, then the detection process will not terminate until timing sector T produces the next such pulse. In the interim, photocells 72 and 73 will detect the binary number represented by the arrangement of marks 68 in a semi-circle of sectors 66 located between timing sectors S and T. Although, in FIG. 8, timing sectors S and T are each shown to have four marks 68 therein while any other sector 66 has at most one mark 68, it should be appreciated that the desired pulse width discrimination can also be achieved using other numbers of marks 68 in each sector 66. For example, timing sectors S and T each may be provided with six marks 68 while any other sector 66 has at most two marks 68. The precise numbers used will depend essentially on the pulse-width discrimination capability of the electronic components used in circuit 80.

Figure 11:
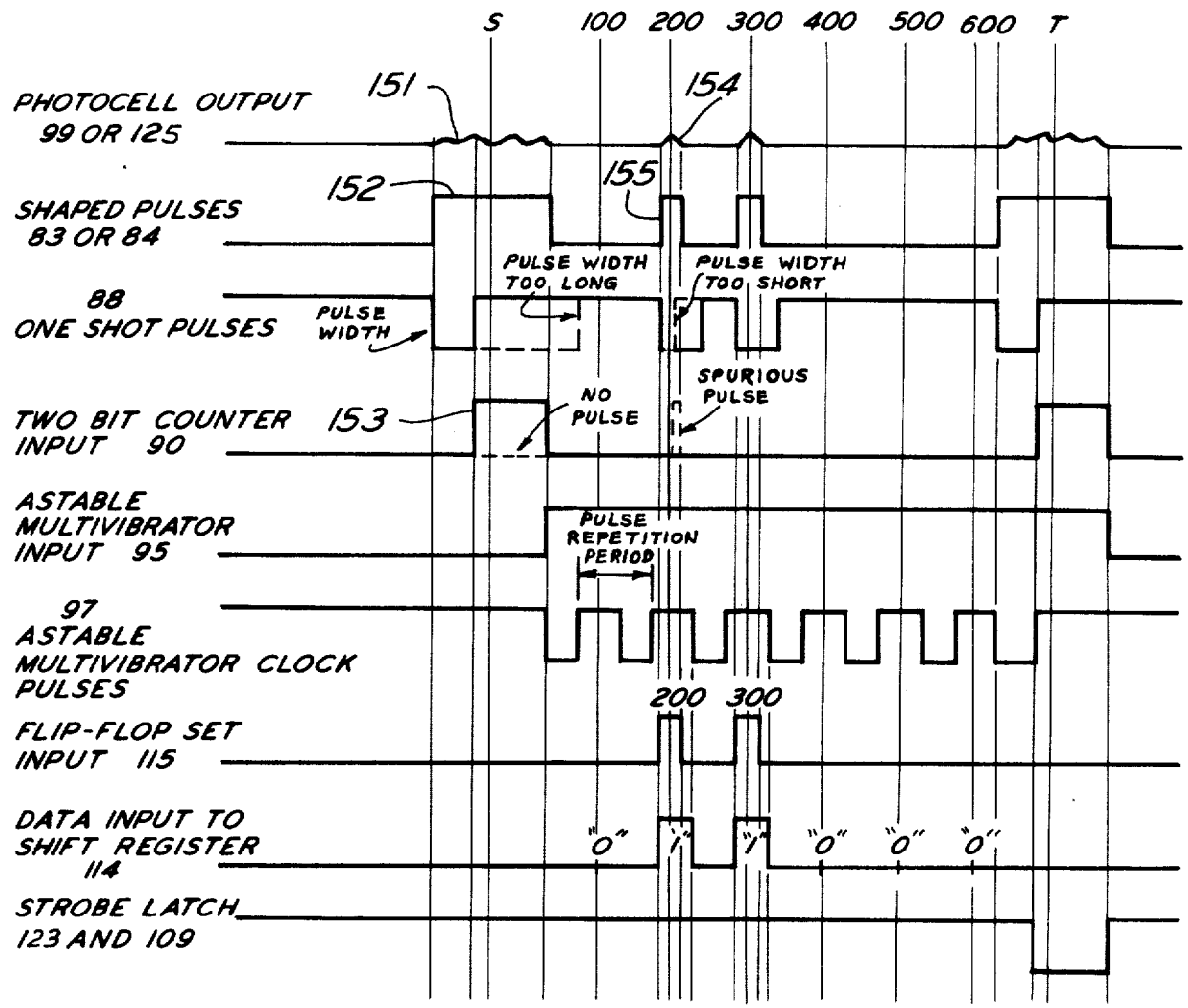
FIG. 11 is a chart of certain signals generated in the electronic control system.

Referring to FIGS. 8, 10 and 11, assume that timing sector S produces the first pulse of relatively long duration (the "long pulse") which initiates the detection process. Thus, as bottle 16 rotates in a counter-clockwise direction, a series of pips will appear on lines 99 and 125 as shown in FIG. 11. With three marks 68 in timing sector S, three pips, designated as 151 in FIG. 11, will serve to initiate the detection process as described further hereinafter.

The three pips 151 are shaped by Pulse Shaping Network 81 or 82 to produce the long pulse on lines 83 or 84. In FIG. 11, the long pulse generated by sector S is designated as 152. Long pulse 152 gates OR gate 85 which produces a digital signal on line 86 corresponding to the pulse waveform on lines 83 or 84. The leading edge of the digital signal on line 86 triggers a One Shot Multivibrator 87 which produces an output pulse (the "one shot pulse") on line 88 in response thereto. The digital output of Multivibrator 87 on line 88 is fed to AND gate 89 in conjunction with the digital output of OR gate 85 on line 86. The digital output of AND gate 89 on line 90 is a pulse designated as 153 in FIG. 10. Due to the signals on lines 86 and 88, pulse 153 has a pulse-width which equals the pulse-width of pulse 152 less the pulse-width of the one shot pulse.

The trailing edge of pulse 153 triggers Two Bit Counter 91 which controls AND gate 94. As well known in the art, each cell in Counter 91 has a regular output and a complementary output. If the regular output is at a 0, the complementary output will be at a 1, and vice-versa. As shown in FIG. 10, the first cell has a regular output $Q_1$, and the second cell a complementary output $\overline{Q_2}$. Initially, Counter 91 is set at zero by a reset switch which may be any suitable switch known in the art. The regular outputs of both cells in Counter 91 will therefore be at 0. When the first pulse 153 on lines 90 is fed to Counter 91, the first cell in Counter 91 registers 1 at terminal $Q_1$ and line 92. At the same time, the second cell in Counter 91 remains in its initial state, that is, at a 0. The complementary output of the second cell, however, will indicate a 1 at complementary terminal $\overline{Q_2}$ and line 93. Accordingly, the output of AND gate 94 on line 95 will rise to a 1 level in response to the 1 levels on lines 92 and 93. The output of AND gate 95 will gate Astable Multivibrator 96. More particularly, Multivibrator 96 will be gated on by the leading edge of the signal appearing on line 95.

When gated on, Astable Multivibrator 96 generates a series of clock pulses on line 97. The clock pulses appearing on line 97, in conjunction with the digital signal on line 86, controls AND gate 101 which sets Flip-Flop 102. More specifically, the output lines 115 of AND gate 101 is connected to the Set Input of Flip-Flop 102. When the signals on lines 97 and 86 are both at the 1 level a pulse will be generated at line 115, as shown in FIG. 11. In response, Flip-Flop 102 will be set and line 114 will rise to a 1 level. The signal on line 114, however, will return to the 0 level when Flip-Flop 102 is reset. As shown in FIG. 11, Flip-Flop 102 is reset at the trailing edge of a clock pulse on line 97. Actually, as shown in FIG. 10, the clock pulses on line 97 are inverted by Inverter 98 and fed, through RC circuit 116, to the Reset Input of Flip-Flop 102. Thus, the leading edge of the inverted clock pulse, which coincides with the trailing edge of the original clock pulse on line 97, resets Flip-Flop 102. RC circuit 116 is a simple holding circuit, well-known in the art, which holds the inverted clock pulses at the digital 0 and 1 levels.

Each pip, designated as 154 in FIG. 11, appearing on lines 99 or 125 due to a single mark 68 in a sector 66 is shaped by Pulse Shaping Network 81 or 84 to produce a pulse of relatively short duration (the "short pulse") 155 on lines 83 or 84. Due to the digital logic described above, each such pulse 155 results in a pulse output on line 114 of Flip-Flop 102, as shown in FIG. 11, but does not trigger the Two Bit Counter 91. The series of pulses appearing on line 114 is shifted into the Data Input of a Six Bit Shift Register 103, conventional in the art, by the inverted clock pulse train appearing at the output of Inverter 98. It should be appreciated that Shift Register 103 may comprise more or less than six bits, depending on the number of sectors 66 in a semi-circle between sectors S and T. The precise number of bits in Shift Registor 103 will equal the number of sectors 66 in a semi-circle.

Corresponding to the distribution of the marks 68 on the sectors 66, the digital signal on line 114 represents a binary word. For example, corresponding to the distribution of the marks 68 on the sectors 66 depicted in FIG. 8, the digital word on line 114 will be 011000, as shown at line 114 in FIG. 11. This word will be shifted into Six Bit Shift Register 103, as already described, and then strobed into Latch 105 by a strobe pulse appearing on line 123. The strobe pulse on line 123 is timed to occur after the Shift Register 103 is fully loaded. Latch 105 may be any suitable memory device known in the art. For example, assuming a Six Blt Register 103, Latch 105 may comprise six flip-flops, each connected to a cell in Register 103 the output of which is strobed into the flip-flop according to principles well-known in the art. At the end of the detection process, the Latch 104 may be reset by any suitable switch.

The digital word stored in Latch 105 is in the binary form and is decoded by Binary to BCD Decoder 106, which may be a conventional device known in the art. The decoder word, in BCD form, is then fed to Mold-Number Display 107 and to Comparator 117, as further described hereinafter.

A digital word identifying a defective mold is preset and stored in Ejector Memory 118 and fed on line 119 to Comparator 117. Ejector Memory 118 may be a matrix of pushbutton switches (not shown) arranged to provide a digitally coded number or word which conforms to the coded number or word generated by Decoder 106. Comparator 117 may be a device conventional in the art which compares the digital word generated by Decoder 106 to the digital word stored in Ejector Memory 118. If the two words match, Comparator 117 sends a control signal 120 to Ejector 121 which engages and ejects the bottle 16 essentially as described in my U.S. Pat. No. 3,387,704. If the words are not identical, then Ejector 121 is not activated and the entire detection process is repeated for the next bottle 16 in procession 12.

The digital word generated by Decoder 106 is also fed to Mold-Number Display 107 which comprises an array of indicator lights for displaying the word according to principles well-known in the art.

Referring to FIG. 10, there is shown a set of Earphones 127 for checking the pulse-width of the one shot pulses on line 88, generated by One Shot Multivibrator 87, and a Latch & Number Display 110 for checking the pulse repetition rate of the pulses on line 97, generated by Astable Multivibrator 96. More specifically, in making an audio check, the procession 12 is halted indefinitely and bottle 16 is spun in place. The pulses appearing on line 90 at the output of AND gate 89 are amplified by Amplifier 112 and fed on line 113 to Earphones 127. Thus, as the bottle 16 spins in place, a series of one shot pulses is generated on line 88 each of which has a pulse-width less than the pulse-width of the long pulse generated on lines 83 or 84 by sectors S or T, but greater than the pulse-width of a short pulse generated by any of the sectors 66 which have only one mark 68 therein. As a result, the pulses appearing on line 90 occur only during a long pulse generated by the sectors S or T. If, however, the pulse-width of a one shot pulse appearing on line 88 exceeds the pulse-width of a long pulse generated by sectors S or T, no pulse will be generated on line 90 and the absence of the pulse will be detected by using Earphones 127. Similarly, if the pulse-width of a one shot pulse appearing on line 88 is less than the pulse-width of a short pulse generated by a mark 68 on a sector 66, then a spurious pulse will be generated on line 90 during the time that a short pulse is generated by a sector 66 and this spurious pulse, appearing at irregular intervals, will be detected by use of the Earphones 127.

The pulse repetition rate of the pulses generated by Astable Multivibrator 96 can be checked to insure that the pulses on line 97 overlap the shaped pulses appearing on lines 83 or 84 so that the required Data Input signal will be generated on line 114. This is accomplished by Five Bit Counter 111 and Latch & Number Display 110 in conjunction with AND gate 108. In particular, the Five Bit Counter 111 counts the number of pulses generated by Astable Multivibrator 96. Although Counter 111 is referred to as having five bits, it should be obvious that the number of bits required depends on the pulse-width repetition frequency of the clock pulses generated by Multivibrator 96 as well as the pulse-width of the shaped pulses on lines 83 or 84, to ensure the proper Data Input signal on line 114 as already explained. Thus, depending on these parameters, Counter 111 may have more or less than five bits. The count maintained by Counter 111 is fed into Latch & Number Display 110 which comprises conventional storage and display circuitry previously referred to with respect to Latch 105 and Mold-Number Display 107. The strobe signal for Latch 105, appearing on line 123, will also appear on line 109 since the inputs to AND gates 104 and 108 are the same, as shown in FIG. 10. The strobe signal on 109, then, strobes the Latch & Number Display 110 to provide a visual indication of the number of pulses generated by Multivibrator 96 during the time that it is gated on by AND gate 95. In this manner, the proper alignment can be maintained between the clock pulses generated by Multivibrator 96 and the shaped pulses appearing on lines 83 or 84 to generate the Data Input pulses in Six Bit Shift Register 104 on line 114.

In summary, then, a transparent bottle 16 is transported by conveyor 14 and caused to rotate about its axis as it moves through the inspection area. During rotation of the bottle 16, a digital number representing the arrangement of marks 68 on the bottom wall 34 of bottle 16 is generated and compared to a preselected digital number which identifies a particular mold. If the numbers match, an Ejector 121 is activated by a control signal 120 to eject bottle 16 from the procession 12.

Although in the preferred embodiment described, the control signal 120 is used to eject a bottle associated with a defective mold, the signal 120 may also be used for other purposes. For example, signal 120 could be used to identify certain bottles which will require special handling, or bottles which are to be shipped to a specific destination, or bottles which are to be selected for test purposes, and so forth.

Further, in the preferred embodiment a Spectra-Physics Model 155 Helium-Neon gas laser having a power of ½ milliwatt and a wavelength of 6328 angstrons was used, however, it should be obvious that other light sources which provide collumated beams of light may also be suitable for use in the invention. Similarly, although in the preferred embodiment an International Rectifier S0505 E8PL silicon photodetector was used, other photodetectors may also be suitable for use in the invention.

The present invention may be embodied in other specific forms without departing from the spirit or essential attributes thereof and, accordingly, reference should be made to the appended claims, rather than to the foregoing specification as indicating the scope of the invention.

I claim:

1. Apparatus for identifying a bottle which is transparent to a laser beam and which is provided with marks on its bottom wall, as the bottle is transported through an inspection area, which comprises;
   a. a linear conveyor for transporting the bottle through the inspection area in a straight line and at a uniform speed;
   b. a first carriage positioned above the conveyor for movement at a uniform speed in synchronism with the bottle as the bottle traverses the inspection area;

c. a laser for generating a laser beam said laser being mounted on said first carriage;

d. a first means for directing the laser beam through the bottom wall of the bottle as the bottle is transported through the inspection area said first directing means being mounted on said first carriage;

e. means for causing relative rotation between the bottle and the laser beam as the bottle is transported through the inspection area so that the beam scans selected portions of the bottom of the bottle;

f. a second carriage positioned adjacent to the conveyor said second carriage being mounted for movement in synchronism with the first carriage and the bottle as the bottle is transported through the inspection area;

g. a sensor for selectively receiving the laser beam after the beam has emerged from the bottom wall of the bottle and for generating a signal in response thereto, the sensor being mounted on the second carriage, the sensor including a photocell for generating an electric signal in response to the laser beam and a mask positioned between the photocell and the bottom wall of the bottle to block the lasar beam from striking the photocell when the beam does not strike a mark on the bottom wall of the bottle;

h. second means positioned below said conveyor for directing the laser beam to the sensor after the laser beam has emerged from the bottom wall of the bottle; and i. an electric control circuit responsive to the signal generated by the sensor, for selectively activating an ejector to eject a bottle whose marks cause a particular signal to be generated by the sensor.

2. Apparatus in accordance with claim 1 wherein the first means includes a pair of aperture plates each provided with a row of holes, the laser being positioned so that the lasar beam passes through one hole in each plate, and a mirror positioned between the aperture plates for reflecting the lasar beam to the bottom wall of the bottle.

3. Apparatus in accordance with claim 1 wherein the linear conveyor includes a stationary support member, and wherein the second means is a mirror securely mounted on the support member and positioned to face the sensor.

4. Apparatus in accordance with claim 3 wherein the means for causing relative rotation between the bottle and the lasar beam includes a first plunger mounted on the first carriage and extending downwardly therefrom, the first plunger being positioned above the bottle for reciprocating motion to and from the neck of the bottle; a pair of spaced neck rollers mounted on the first plunger and positioned to rollably engage the neck of the bottle and to present the bottle from tipping over as the bottle is rotated while being transported by the conveyor through the inspection area; a rotator belt positioned alongside the conveyor adjacent to the inspection area for rotating the bottle while the bottle overhangs the edge of the conveyor closest to the sensor; a second plunger mounted on the second carriage for lateral reciprocating motion to and from the bottle as the bottle is transported through the inspection area; and a pair of spaced plunger rollers mounted on the second plunger for rotatably engaging the bottle and urging it into rotatable contact with the rotator belt, whereby movement of the rotator belt causes relative rotation between the bottle and the lasar beam.

5. Apparatus in accordance with claim 1 including an ejector for ejecting said bottle, an ejector memory for storing an electric signal representing a preselected digital number, and wherein said control circuit includes means for digitally encoding said signal generated by the sensor, and means for comparing the stored signal to said encoded signal and for activating the ejector to eject said bottle when the stored signal and said encoded signal are identical.

6. Apparatus comprising:
   means for conveying bottles made from a material transparent to a laser beam;
   means for directing a lasar beam through a circumferential zone of said bottle while the bottle is moving;
   means for causing relative rotation of said bottle with respect to aid lasar beam while said bottle is moving;
   means for detecting the presence or absence of spreading of said beam by prism-like marks on the bottle per circumferential segments in the zone of the bottle; and
   means coupled to said detecting means for generating an electric siganl in response to the detection of spreading and absence of spreading of said beam.

7. A method for identifying a bottle which is transparent to a laser beam, as the bottle is transported through an inspection area, which comprises the steps of:
   forming marks on the bottom wall of the bottle, each mark being shaped to cause a laser beam to spread as the beam strikes the mark and leaves the bottle;
   generating a laser beam;
   directing the laser beam through the bottom wall of the bottle as the bottle is transported through the inspection area;
   causing relative rotation between the bottle and the laser beam so that the beam scans selected positions of the bottom of the bottle as the bottle is transported through the inspection area; and
   generating an electric signal in response to the laser beam only when the beam strikes a mark and passes through the bottom wall of the bottle, by blocking the laser beam from striking a photocell when the laser beam does not strike a mark and by allowing the beam to strike the photocell when the beam strikes a mark.

8. A method in accordance with claim 7 wherein the step of directing the laser beam through the bottom wall of the bottle includes adjusting the path of the laser beam so that the beam strikes a selected portion of the bottom wall of the bottle.

9. A method in accordance with claim 7 including the steps of storing an electric signal representing a preselected digital number; encoding the electric signal generated in step (e) to form a digital signal representing a digital number corresponding to the distribution of the marks on the bottom wall of the bottle; comparing the stored signal to the encoded signal; and generating a signal for activating the ejector when the stored signal and the encoded signal are identical.

10. A method of identifying a container which is transparent to a laser beam and which contains prism-like marks arranged on circumferential segments of a wall thereof, comprising: transporting said container through an inspection area directing a laser beam at a portion of said container containing said marks while rotating one of said beam and container about the axis of the container as the container is transported through the inspection area;

passing said beam directly through portions of the container lacking said marks and spreading said beam by said marks; and detecting the presence and absence of the spreading of said beam per circumferential segment of said container and generating a binary signal as a function thereof as the container is transported through the inspection area;

11. A method in accordance with claim 9 including stopping and starting said detecting step by causing a plurality of adjacent marks on said bottle to spread said beam continuously as the beam passes through a circumferential segment containing said plurality of adjacent marks.

12. A method of identifying a bottle which is transparent to a laser beam and which contains two identical sets of prism-like marks arranged in circumferential segments of a wall thereof, comprising:

transporting said bottle through an inspection area;

directing a laser beam at both sets of said marks while rotating one of said beam and bottle about the axis of the bottle as the bottle is transported through the inspection area;

passing said beam directly through portions of the bottle lacking said marks and spreading said beam by said marks; and detecting the presence and absence of the spreading of said beam per circumferential segment of said bottle and generating a binary signal as a function thereof as the bottle is transported through the inspection area.

13. Apparatus for identifying a container, comprising:

means for directing a laser beam through a circumferential zone of said container;

means for causing relative rotation of said container with respect to said laser beam;

means for detecting the presence or absence of spreading of said beam by prism-like marks on the container per segments of said circumferential zone of the container; and means coupled to said detecting means for generating an electric signal in response to the detection of spreading and absence of spreading of said beam.

14. A method of identifying a container, comprising:

directing a laser beam through a circumferential zone of said container;

causing relative rotation between said container and said laser beam;

detecting the presence or absence of the spreading of said beam by prism-like marks on the container per segments of said circumferential zone of the container; and generating an electric signal in response to the detection of spreading and absence of spreading of said beam.

* * * * *